US00PP18361P2

(12) United States Plant Patent
White

(10) Patent No.: US PP18,361 P2
(45) Date of Patent: Dec. 25, 2007

(54) ***DAPHNE* PLANT NAMED 'BLAFRA'**

(50) Latin Name: *Daphne×transatlantica*
Varietal Denomination: Blafra

(76) Inventor: Anthony Robin White, Blackthorn Nursery Kilmeston, Alresford, Hampshire, SOZ4 ONL (GB)

( * ) Notice: Subject to any disclaimer, the term of this patent is extended or adjusted under 35 U.S.C. 154(b) by 29 days.

(21) Appl. No.: 11/479,800

(22) Filed: Jun. 29, 2006

(51) Int. Cl.
*A01H 5/00* (2006.01)

(52) U.S. Cl. ..... Plt./226
(58) Field of Classification Search ..... Plt./226
See application file for complete search history.

(56) References Cited

PUBLICATIONS

UPOV–ROM GTITM, Plant Variety Database, 2007/01, GTI Jouve Retrieval Software, citation for 'Blafra'.*

* cited by examiner

*Primary Examiner*—Kent Bell
*Assistant Examiner*—S. B. McCormick-Ewoldt

(57) ABSTRACT

A new cultivar of *Daphne* plant named 'BLAFRA' that is characterized by open-branched habit, semi-glossy dark-green foliage, and intensely fragrant white flowers with an orange-yellow "eye" comprised of orange-yellow anthers. In combination these traits set 'BLAFRA' apart from all other existing varieties of *Daphne* known to the inventor.

2 Drawing Sheets

Genus: *Daphne.*
Species: *×transatlantica.*
Denomination 'BLAFRA'.

BACKGROUND OF THE INVENTION

The present invention relates to a new and distinct cultivar of *daphne* plant grown as an ornamental shrub for use in container and the landscape. The new variety is known botanically as *Daphne×transatlantica* and will be referred to hereinafter by the cultivar name 'BLAFRA'.

In clarification of the nomenclature, the inventor denotes the epithet *×transatlantica* in recognition of plants found in commerce throughout Europe and the United States, which are generally described as evergreen, and described as varieties of *Daphne caucasica.* In actuality these have been derived from a chance cross between the true species *Daphne caucasica,* and *Daphne collina,* an Italian species growing in California. The true species of *Daphne caucasica* is deciduous except in climates such as that of coastal California.

'BLAFRA' is a seedling plant selection arising from deliberate cross-pollination of an unnamed individual *Daphne caucasica* (the true species) as the female parent, and an unnamed individual *Daphne collina* as the male parent. Cross-pollination was conducted by the inventor at the inventor's nursery in Hampshire, England. The seed parent *Daphne caucasica* is the true species, hardy, deciduous, and one of the parents of the popular *Daphne× burkwoodii* hybrids.

In 1995 the inventor fertilized *Daphne caucasica* with pollen obtained from *Daphne collina.* Seed was germinated from the resulting cross in March 1996. One seedling flowered and was selected, then grown on. This seedling has since proved to resemble plants in commerce described as *Daphne caucasica* rather than the true species of *Daphne caucasica.* The inventor's hybrid of *Daphne caucasica× collina,* here termed *Daphne×transatlantica* and known as 'BLAFRA' has provided further indication that plants described as *Daphne caucasica* are accurately described as *Daphne caucasica×collina,* now termed *Daphne× transatlantica.*

The new *Daphne* variety named 'BLAFRA' forms a neat round open-branched semi-evergreen shrub. 'BLAFRA' exhibits dark-green, semi-glossy leaves, and intensely fragrant white flowers with an orange-yellow "eye" in the center formed by the bright orange-yellow anthers. When night temperatures become cool the flowers blush pink-purple. Unusually for varieties of *Daphne* known to the inventor, 'BLAFRA' exhibits an ability to bear flowers on its new summer growth. Mature plants reach a breadth of 90 centimeters and a height ranging from 75–90 centimeters. 'BLAFRA' performs best in full sun and well-draining acid or alkaline soil which is provided with adequate but not excess water. Once established 'BLAFRA' is drought tolerant, however, dry conditions can reduce summer bloom. Flowering occurs April through May and irregularly through the summer months and until November. 'BLAFRA' is hardy to USDA Zone 5.

The new *Daphne* variety named 'BLAFRA' is distinguishable from the female parent in habit, mature height, axillary shoots, and fruit color. The female parent *Daphne caucasica* exhibits upright habit to 2 meters in height, fruit that is black or red in color, and axillary shoots on second year wood. In comparison, 'BLAFRA' exhibits semi-upright habit reaching 75–90 centimeters in height, orange fruit, and no axillary shoots on second year wood. 'BLAFRA' is distinguishable from the male parent in habit, mature height, leaf surface, and leaf appearance. The male parent *Daphne collina* exhibits compact dense habit, reaching 60 cm. in height, and has leaves that are highly glossy on the top surface with silky pubescence on the underside surface. In comparison 'BLAFRA' exhibits open-branched habit, a mature height ranging from 75–90 centimeters, and has leaves that are semi-glossy on the top surface, and slightly hairy on the underside surface.

The closest comparison plant known to the inventor is *Daphne caucasica* (actually *Daphne×transatlantica*) 'Jim's Pride' (unpatented). 'BLAFRA' is distinguishable from the comparison plant by leaf dimensions, leaf texture, flower dimensions, flower color, and flower shape. The comparison plant 'Jim's Pride' exhibits long wide leathery leaves, and medium-size white flowers. In comparison 'BLAFRA' exhibits long narrow sub-coriaceous leaves, large white flowers with flat spreading lobes, and faint pink-purple blush.

'BLAFRA' was first asexually propagated in 1996 using the method of semi-ripe cuttings. Asexual propagation was conducted by the inventor at the inventor's nursery in Hampshire, England. Since that time under careful observation, 'BLAFRA' has been determined stable, uniform, and reproduces true to type in successive generations of asexual propagation.

The inventor filed an application for a grant of European Community Plant Breeder's Rights for 'BLAFRA' on Jul. 2, 2004, Serial Number 2004/1214.

The first sale or distribution to the public took place on or after Aug. 1, 2005 when plants of 'BLAFRA' were sold to a garden center in Suffolk, England.

SUMMARY OF THE INVENTION

The following traits have been repeatedly observed and represent the distinguishing characteristics of the new *Daphne* variety known as 'BLAFRA'. These traits in combination distinguish 'BLAFRA' from all other existing varieties of *Daphne* known to the inventor. 'BLAFRA' has not been tested under all possible conditions and phenotypic differences may be observed with variations in environmental, climatic, and cultural conditions, however, without any variance in genotype. Growing requirements are similar to the species.

1. 'BLAFRA' exhibits open-branched semi-upright habit.
2. 'BLAFRA' exhibits neat, rounded form and shape.
3. 'BLAFRA' exhibits semi-glossy dark-green foliage.
4. 'BLAFRA' exhibits intensely fragrant white flowers with an orange-yellow "eye" formed by bright orange-yellow anthers.
5. The flowers of 'BLAFRA' blush pink-purple following cool night temperatures.
6. 'BLAFRA' bears flowers on new summer growth.
7. 'BLAFRA' is a semi-evergreen shrub grown for use in container or the landscape.
8. 'BLAFRA' is asexually propagated by the method of semi-ripe cuttings.
9. 'BLAFRA' reaches 75–90 cm. in height and 90 cm. in width at maturity.
10. 'BLAFRA' blooms in spring and irregularly through summer and fall.
11. 'BLAFRA' exhibits orange fruit after flowering.
12. 'BLAFRA' is hardy to USDA Zone 5.

BRIEF DESCRIPTION OF THE DRAWINGS

The accompanying color drawings illustrate the overall appearance of the new *Daphne* variety named 'BLAFRA' showing colors as true as it is reasonably possible to obtain in colored reproductions of this type.

The drawing labeled

The drawing labeled

Figure 1:
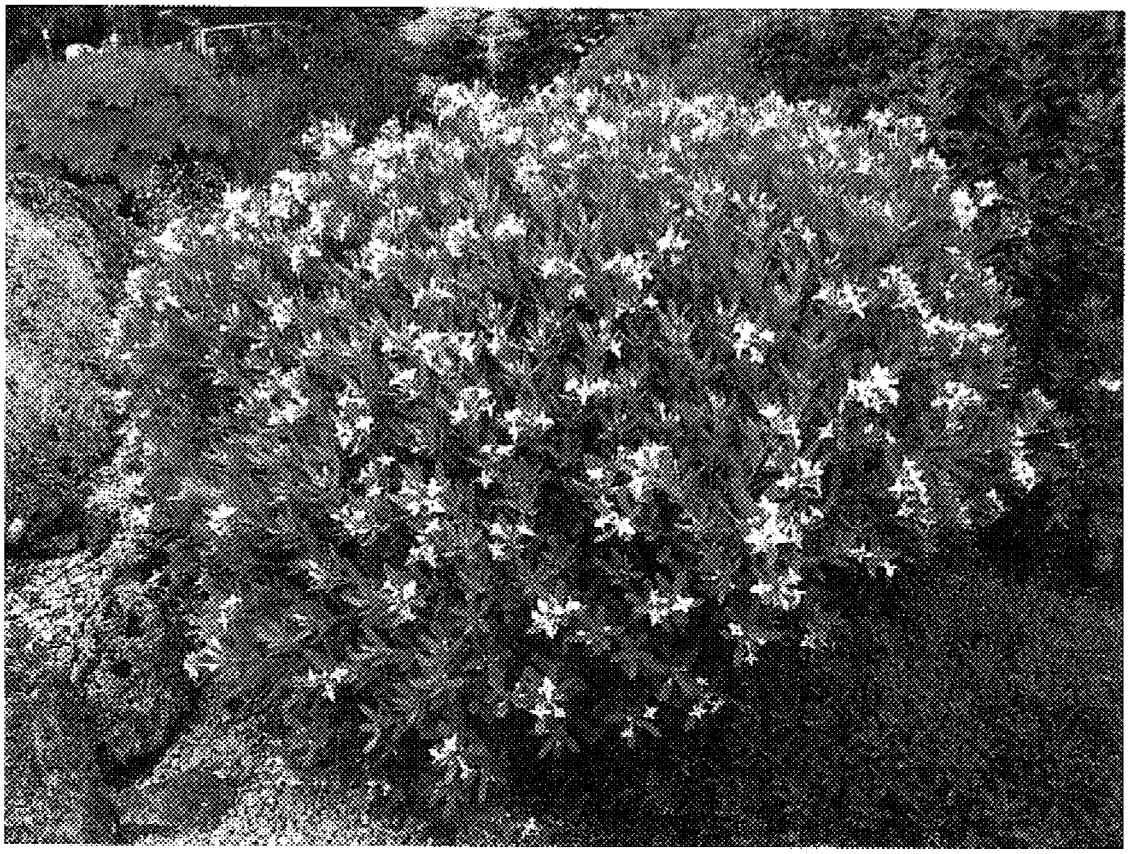
FIG. 1 depicts an individual whole plant from a side perspective illustrating habit.
Figure 2:
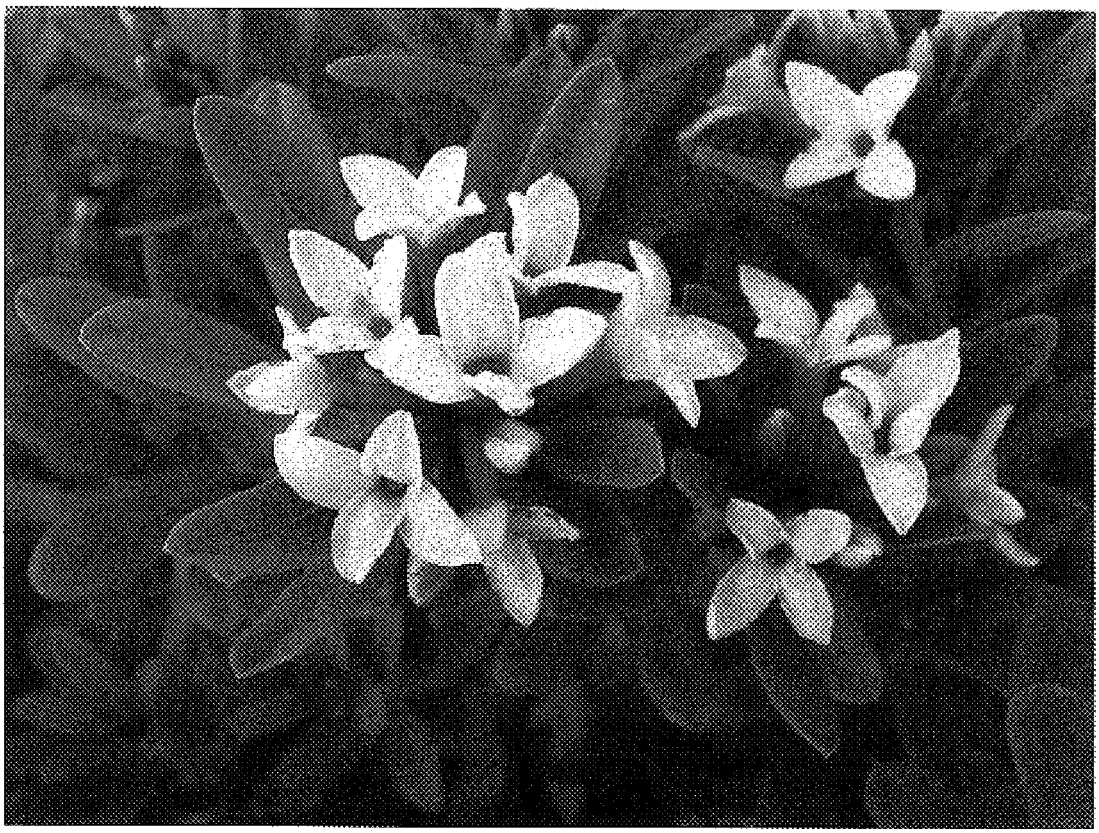
FIG. 2 is a close-up of foliage and flower.

Color in the drawings may differ from color values cited in the detailed botanical description, which accurately describe the actual color of the new *Daphne* variety named 'BLAFRA'. Drawings labeled FIG. 1 and FIG. 2 were made using conventional techniques and although foliage colors may appear different from actual colors due to light reflectance, they are as accurate as possible by conventional photography.

BOTANICAL DESCRIPTION OF THE PLANT

The following is a detailed description of the new *Daphne* cultivar named 'BLAFRA'. Data was collected in Arroyo Grande, Calif. from plants grown out-of-doors in 1-liter containers. Phenotypic differences may be observed with variations in environmental, climatic, and cultural conditions, without however, any difference in genotype. Color determinations are in accordance with the 2001 edition of The Royal Horticultural Society Colour Chart except where general color terms of ordinary dictionary significance are used. The growing requirements are similar to the species.

Botanical classification: *Daphne×transatlantica* 'BLAFRA'.
Family: Thymelaeaceae.
Genus: *Daphne.*
Species: *×transatlantica.*
Denomination: 'BLAFRA'.
Common name: *Daphne.*
Plant type: Shrub.
Plant use: For container and landscape.
Plant parentage: *Daphne×transatlantica* 'BLAFRA' is a seedling selection arising from deliberate cross-pollination of the following parents:
*Female parent.*—An unnamed plant of *Daphne caucasica* (true species).
*Male parent.*—An unnamed plant of *Daphne collina.*
Plant vigor: Low.
Plant shape: Rounded.
Branching habit: Open-branching.
Dimensions at maturity: 75 cm. to 90 cm. in height and 90 cm. in width.
Plant hardiness: USDA Zone 5.
Bloom season: Spring, summer, fall.
Asexual propagation method: Semi-ripe cuttings taken from mid-May onwards in succession.
Growth habit: Semi-upright.
Growing considerations: Can be grown in container for several years provided diameter exceeds 12-inches and surface of compost is mulched to avoid high temperatures.
Root system: Fibrous.
Sunlight: Full sun.
Soil: Acidic or alkaline well-draining soil.
Water: Provide adequate but not excess water, taking care to consider that plant is drought tolerant once established, however, summer bloom is reduced by very dry conditions.
Fertilizer: Benefits from regular feeding but avoid excess which may result in lax growth and increased risk of disease.
Time to initiate roots: 6–8 weeks to develop roots on an initial cutting.

Crop time: 13–14 months to produce commercial container plant.
Special considerations: All parts are poisonous if ingested.
Pest susceptibility: Inspect regularly for aphids.
Disease susceptibility: *Botrytis* and leaf spot when exposed to prolonged wet conditions.
Stem:
*Stem shape* (*first year*).—Cylindrical.
*Stem surface* (*first year*).—Pubescent with appressed hairs.
*Pubescence color.*—155B.
*Stem color* (*first year*).—144A.
*Stem shape* (*after first year*).—Terete.
*Stem color* (*after first year*).—200B.
*Stem surface* (*after first year*).—Glabrous.
*Stem length* (*1-liter container plant*).—Average is 21 cm.
*Stem diameter* (*1-liter container plant*).—Average is 3 mm.
*Internodes* (*1-liter container plant*).—Average is 0.75 cm.
Foliage:
*Foliage type.*—Semi-evergreen.
*Leaf arrangement.*—Alternate.
*Leaf division.*—Simple.
*Leaf shape.*—Narrowly elliptic.
*Leaf texture.*—Sub-coriaceous.
*Leaf appearance* (*adaxial surface*).—Semi-glossy.
*Leaf appearance* (*abaxial surface*).—Matte.
*Leaf apex.*—Mucronulate.
*Leaf base.*—Attenuate.
*Leaf attachment.*—Combination of shortly petiolate and sessile.
*Leaf margin* (*first year*).—Ciliate margins on first year growth.
*Leaf margin* (*after first year*).—Entire.
*Leaf surface* (*adaxial*).—Glabrous.
*Leaf surface* (*abaxial*).—Puberulent.
*Puberulence color.*—155B.
*Leaf length.*—Average is 4.70 cm.
*Leaf width.*—Average is 1.10 cm.
*Leaf color* (*adaxial surface*).—139A.
*Leaf color* (*abaxial surface*).—138B.
*Venation* (*adaxial and abaxial surfaces*).—Prominent mid-vein.
*Vein color* (*adaxial surface*).—139A.
*Vein color* (*abaxial surface*).—138A.
*Petiole dimensions.*—2 mm. in length and 1.75 mm. in width.
*Petiole surface.*—Glabrous.
*Petiole color.*—144C.
*Foliar fragrance.*—None observed.
Inflorescence:
*Inflorescence type.*—Axillary head.
*Inflorescence dimensions.*—3 cm. in length and 4 cm. in width.
*Flower quantity.*—Up to 10 flowers per inflorescence.
*Flower bloom time.*—April through May and irregularly through summer months and until November. Flowers are borne on new summer growth.
*Flower shape.*—Salverform.
*Flower dimensions.*—1.40 cm. in diameter and 1.50 cm. in depth.
*Petals.*—Apetalous.
*Bud color* (*in tight bud*).—N74D.
*Bud dimensions.*—2 cm. in length and 0.40 cm in diameter.
*Bud shape.*—Scepter-shaped.
*Bud surface.*—Densely pubescent.
*Bud apex.*—Acute.
*Bud base.*—Rounded.
*Calyx.*—Perianth tube: Cylindrical. Perianth tube color: 150D and N74D. Perianth tube dimensions: 1 cm. in length and 0.25 cm. in diameter. Perianth tube surface (exterior): Hairy. Perianth tube surface (interior): Frost-like. Perianth lobes: 4 in number. Perianth lobes fused or unfused: Unfused. Perianth lobe form: Petaloid. Perianth lobe surface (adaxial): Glabrous. Perianth lobe surface (abaxial): Puberulent with appressed hairs. Perianth lobe color (adaxial and abaxial surfaces): 157D. Perianth lobe length: 9 mm. Perianth lobe width: 5 mm. Perianth lobe shape: Narrowly ovate. Perianth lobe apex: Acute. Perianth lobe margin: Semi erect and cuculate at tips. Perianth lobe appearance: Crystalline.
*Pedicel dimensions.*—3 mm. in length and 1 mm. in diameter.
*Pedicel color.*—144B.
*Pedicel shape.*—Cylindrical.
*Pedicel surface.*—Densely pubescent.
*Pubescence color.*—155B.
*Flower fragrance.*—Intense perfume fragrance.
*Special considerations.*—Pink-purple blush following cool night temperatures.
Reproductive organs:
*Stamens.*—8 in two whorls of 4 each.
*Stamen attachment.*—Adnate to interior of perianth tube.
*Stamen length.*—1 mm.
*Stamen color.*—155B.
*Anther dimensions.*—1 mm. in height and less than 0.50 mm. in width.
*Anther color.*—17A.
*Pistil.*—None observed.
*Stigma shape.*—Discoid capitate.
*Stigma attachment.*—Sessile.
*Stigma surface.*—Hispid.
*Stigma color.*—178D.
*Stigma height.*—Less than 0.50 mm.
*Ovary shape.*—Sub-globose.
*Ovary dimensions.*—1.50 mm in diameter and 2 mm. in height.
*Ovary color.*—150D.
*Ovary attachment.*—Shortly stalked.
*Ovary surface.*—Appressed pubescence.
*Ovary position.*—Superior.
Fruit:
*Fruit shape.*—Globose.
*Fruit color.*—N170A.
*Fruit texture.*—Fleshy.

It is claimed:

1. A new and distinct variety of *Daphne* plant named 'BLAFRA' as described and illustrated herein.

* * * * *